(12) United States Patent
Sanderson et al.

(10) Patent No.: US 6,350,871 B1
(45) Date of Patent: Feb. 26, 2002

(54) CRYSTALLIZATION OF 2,4,6,8,10,12-HEXANITRO-2,4,6,8,10,12-HEXAAZATETRACYCLO[5.5.0.0⁵,⁹0³,¹¹]-DODECANE

(75) Inventors: Andrew J. Sanderson, North Ogden; Richard S. Hamilton, Bear River City; Kirstin F. Warner, Ogden, all of UT (US)

(73) Assignee: Alliant Techsystems Inc., Edina, MN (US)

( * ) Notice: Subject to any disclaimer, the term of this patent is extended or adjusted under 35 U.S.C. 154(b) by 0 days.

(21) Appl. No.: 09/813,687

(22) Filed: Mar. 21, 2001

Related U.S. Application Data

(60) Provisional application No. 60/193,468, filed on Mar. 31, 2000.

(51) Int. Cl.⁷ ............................................. C07D 255/04
(52) U.S. Cl. ...................................... 540/554; 540/475
(58) Field of Search ......................................... 540/554

(56) References Cited

U.S. PATENT DOCUMENTS

| | | | |
|---|---|---|---|
| 5,099,008 A | 3/1992 | Voigt, Jr. et al. | 540/475 |
| 5,587,553 A | 12/1996 | Braithwaite et al. | 149/19.6 |
| 5,693,794 A | 12/1997 | Nielsen | 549/554 |
| 5,712,511 A | 1/1998 | Chan et al. | 264/3.4 |
| 5,739,325 A | 4/1998 | Wardle et al. | 540/554 |
| 5,750,921 A | 5/1998 | Chan et al. | 149/19.92 |
| 5,874,574 A | 2/1999 | Johnston et al. | 540/475 |
| 5,936,196 A | 8/1999 | Dawson | 149/92 |
| 5,942,722 A | 8/1999 | Dawson | 149/92 |
| 5,973,149 A | 10/1999 | Bescond et al. | 544/345 |

FOREIGN PATENT DOCUMENTS

EP   0 913 374 A1   5/1999

*Primary Examiner*—John M. Ford
(74) *Attorney, Agent, or Firm*—Sullivan Law Group

(57) ABSTRACT

CL-20 is crystallized from a solution containing a CL-20 organic solvent and a CL-20 non-solvent miscible with the solvent. The CL-20 non-solvent is a nitrate ester, preferably poly(glycidyl nitrate) and/or triethyleneglycol-dinitrate, although other nitrate ester plasticizers having acceptable volatilities and impact sensitivities can be used. The solution is saturated with CL-20, and CL-20 is then crystallized from the saturated solution by adding ε-polymorph CL-20 crystalline seeds to the solution and evaporating off the CL-20 solvent, preferably under vacuum. The nitrate ester non-solvent is then separated from the crystalline CL-20, such as by filtration of the CL-20 crystals or by diluting the slurry of non-solvent and CL-20 with an environmentally acceptable solvent that is miscible with the non-solvent but in which the CL-20 is insoluble.

26 Claims, No Drawings

CRYSTALLIZATION OF 2,4,6,8,10,12-HEXANITRO-2,4,6,8,10,12-HEXAAZATETRACYCLO[5.5.0.05,903,11]-DODECANE

CROSS-REFERENCE TO RELATED APPLICATION

The benefit of priority of claimed of U.S. Provisional Application No. 60/193,468 filed in the U.S. Patent & Trademark Office on Mar. 31, 2000, the complete disclosure of which is incorporated herein by reference.

GOVERNMENT LICENSING CLAUSE

The U.S. Government has a paid-up license in this invention and the right in limited circumstances to require the patent owner to license others on reasonable terms as provided for by the terms of contract N00174-99-C-0030 awarded by the Indian Head Division of the Naval Air Warfare Center (NAWC).

BACKGROUND OF THE INVENTION

1. Field of the Invention

The present invention relates to an improved method of crystallizing 2,4,6,8,10,12-hexanitro-2,4,6,8,10,12-hexaazatetracyclo[$5.5.0.0^{5,9}0^{3,11}$]-dodecane, also known as hexanitrohexaazaisowurtzitane, hereinafter referred to as CL-20. In particular, this method involves crystallization of CL-20 as an epsilon-polymorph.

2. Description of the Related Art

For most existing propellant and weapons systems, the most critical ingredient in terms of propulsive and explosive performance is the oxidizer. CL-20, with its substantial increase in performance output, is an organic oxidizer presenting significant opportunities in terms of energy capabilities for propellants and explosives. For example, the use of CL-20 as the energetic filler in weapons systems may provide increased anti-armor penetration, enhanced missile payload velocity and flight, increased underwater torpedo effectiveness and lethality, and improved gun propellant impetus.

The performance of CL-20 in propellant and weapon systems is highly dependent upon the crystal polymorph of CL-20. CL-20 has several different crystal polymorphs, the most preferred of which is a high density phase known in the art and referred to herein as the $\epsilon$-polymorph (or epsilon-polymorph) of CL-20. The $\epsilon$-polymorph of CL-20 is preferred because of the high energetic performance and relatively low sensitivity attributable to the $\epsilon$-polymorph. However, many conventional CL-20 synthesis techniques produce $\alpha$-polymorph as the predominant crystal polymorph. The $\alpha$-polymorph has a much lower density that the $\epsilon$-polymorph. For these reasons, CL-20 synthesized by many conventional techniques must be subjected to re-crystallization in order to increase the concentration of the $\epsilon$-polymorph.

Conventionally, CL-20 has been crystallized using chloroform to precipitate CL-20 from ethyl acetate. Chloroform has been found to produce consistently and reproducibly the desirable $\epsilon$-polymorph of CL-20. However, one disadvantage to using chloroform is that defects are often found in the crystalline structure of $\epsilon$-polymorph CL-20 crystallized with chloroform. Another disadvantage of this conventional technique is that chloroform and ethyl acetate cannot be separated effectively and efficiently by distillation, thus complicating the reuse of these solvents. Because the chloroform cannot be easily reused, a continual discharge of a chlorinated waste stream must be disposed of in an environmentally acceptable manner. As a chlorinated solvent, chloroform may potentially contribute to ozone depletion, thus complicating waste disposal of chloroform and other chlorinated solvents. It is, therefore, advantageous to crystallize CL-20 into the $\epsilon$-polymorph with solvents that can be recycled within the crystallization process without producing a discharge of chlorinated solvents.

A CL-20 crystallization technique that avoids the use of chloroform and other chlorinated solvents and non-solvents is disclosed in U.S. Pat. No. 5,874,574, in which CL-20 is dissolved in a solution containing a CL-20 solvent, such as ethyl acetate, and water to form an aqueous phase and a wet solvent phase. The wet CL-20 solvent phase is then dried by azeotropicly. A low density CL-20 non-solvent is then added to the dry CL-20 solvent phase to cause crystallization of $\epsilon$-polymorph CL-20. The CL-20 crystals are then separated from the non-solvent and the solvent by adding sufficient water to displace the non-solvent and the solvent from the surface of the $\epsilon$-polymorph CL-20 crystals. Although high recoveries of $\epsilon$-polymorph CL-20 are reported in U.S. Pat. No. 5,874,574, it is also disclosed that relatively large quantities of water are needed to separate the nonsolvent and solvent from the CL-20 crystals. In some cases, the quantities of water can require larger separation and recycling equipment, thus increasing the capital expenditures and operating costs of this process.

It would therefore be a significant improvement in the art to provide a method for crystallizing high concentrations of $\epsilon$-polymorph CL-20 having high quality and little defects without relying on chlorinated solvents and non-solvents or large water separation and recycling equipment needed by conventional processes.

SUMMARY OF THE INVENTION

It is, therefore, an object of this invention to overcome a long-felt need in the art by providing a method that produces $\epsilon$-polymorph (epsilon-polymorph) CL-20 possessing excellent quality in high yields, yet which method is environmentally friendly and more economically efficient than known methods.

In accordance with the principles of this invention, the above and other objects are attained by a method in which CL-20 is crystallized from a solution comprising at least one CL-20 organic solvent and a CL-20 non-solvent comprising at least one nitrate ester, in particular poly(glycidyl nitrate) and/or a nitrate ester plasticizer. The nitrate ester is preferably poly(glycidyl nitrate) and/or triethyleneglycol-dinitrate, although other nitrate plasticizers having acceptable volatilities and impact sensitivities can be used. The solution is saturated with CL20, and CL-20 is crystallized from the saturated solution by, for example, adding $\epsilon$-polymorph CL-20 crystalline seeds to the solution and evaporating off the CL-20 solvent. Evaporation is preferably conducted under vacuum or with the aid of a similar technique for removing the solvent vapor, such as blowing a dry gas over the evaporator. The nitrate ester non-solvent and any non-evaporated remnants of the solvent are then separated from the crystalline CL-20 by a suitable solid-liquid separation technique, such as by filtration of the CL-20 crystals. If necessary or desirable, prior to solid-liquid separation the nitrate ester non-solvent can be diluted, and its viscosity lowered, by diluting the slurry of non-solvent and CL-20 with a solvent that is miscible with the non-solvent but in which the CL-20 is insoluble. The CL-20 can then be washed.

Advantageously and unexpectedly, the crystallization of the CL-20 in the nitrate ester non-solvent produces high quality ε-polymorph CL-20 crystals that may have few crystal defects and exhibit enhanced energetic performance and lower impact sensitivity compared to CL-20 crystallized by known techniques. Additionally, the solution in which the CL-20 is dissolved and eventually crystallized comprises a mixture of an environmentally acceptable solvent and a non-solvent free of chlorinated compounds and other compounds regulated as Hazardous Air Pollutants (HAPs) under the Clean Air Act. Both the solvent and non-solvent can be recycled for further processing without further treatment or purification.

The CL-20 crystallized by this method is excellent for use in propellant, explosive, and pyrotechnic formulations.

Other objects, aspects, and advantages of this invention will become more apparent to those skilled in the are upon reading the specification and appended claims, which explain the principles of this invention.

DETAILED DESCRIPTION OF PREFERRED EMBODIMENTS AND METHODS OF THE INVENTION

Crystallization of CL-20 in accordance with this novel method is performed in a solution comprising at least one CL-20 organic solvent and a CL-20 non-solvent comprising at least one CL-20 nitrate ester that is miscible with the solvent.

As referred to herein, the term "CL-20 solvent" includes solvents that have a relatively high CL-20 solubility of at least 20% weight/volume (g/ml) of CL-20 in the solvent. The CL-20 solvent preferably has a relatively low boiling point to permit evaporation of the CL-20 solvent at temperatures not exceeding 60° C. Solvent evaporation can be, and preferably is, conducted under a vacuum or in the presence of a blowing dry gas or the like to remove the solvent vapor. Ethyl acetate is currently the preferred solvent because of its low boiling point and environmental acceptability compared to chlorinated solvents. Other non-halogenated CL-20 solvents suitable for use in this invention include other alkyl acetates, such as methyl acetate, n-propyl acetate, and iso-propyl acetate; ketones such as acetone, methyl ethyl ketone; cyclic ethers such as tetrohydrofuran; nitromethane; and acetonitrile. Preferably, an effective amount of the organic solvent is included in the solution mixture to completely dissolve the CL-20 ingredient into the solution prior to commencement of crystallization.

Nitrate esters that are suitable for use in the present invention as the CL-20 non-solvent include those nitrate esters having relatively low vapor pressures, low volatilities, and low impact sensitivities for nitrate esters. The selection of nitrate esters meeting these criteria prevents evaporation of the nitrate ester non-solvent as the CL-20 solvent is evaporated, even when the evaporation of the CL-20 solvent is conducted under vacuum or with the aid of a dry gas. Evaporation of the nitrate ester is desirably avoided due to the hazardous associated with evaporation of nitrate esters. The non-solvent selected for use in this invention is preferably poly(glycidyl nitrate) (PGN) and/or the nitrate ester plasticizer triethyleneglycol-dinitrate (TEGDN), which may be used alone or in combination with each other or other non-solvents. Other suitable nitrate ester plasticizers, such as butanetrioltrinitrate (BTTN) and diglycerol tetranitrate (DGTN), can also be used, although these alternative nitrate ester plasticizers are less preferred due to their higher impact sensitivities. Although other nitrate plasticizers may be used, care should be taken due to their high vapor pressures and volatilities, which can cause these nitrate esters to evaporate with the CL-20 solvent and complicate separation of the solvent and non-solvent.

The weight ratio of nitrate ester non-solvent(s) to CL-20 is preferably not less than about 4:1, and more preferably is in a range of from about 5:1 to about 8:1. The presence of less than an about 4:1 ratio of nitrate ester non-solvent to CL-20 can lead to the formation of defects in the CL-20 during crystallization. On the other hand, operating at a ratio of more than about 8:1 is economically inefficient inasmuch as such high ratios may require longer processing times, more man-power, and larger operating equipment.

The nitrate ester non-solvents can be used alone or in combination with other non-solvents known in the art. In the event that the poly(glycidyl nitrate) or nitrate ester plasticizer(s) are used with known non-solvents, the non-solvents preferably have poor CL-20 solubility of not more than 5% weight/volume (g/ml), more preferably not more than 1% weight/volume (g/ml), of CL-20 in the non-solvent. The CL-20 non-solvent preferably possesses low volatility and has a boiling point higher than that of the solvent, thus permitting the solvent to be separated from the CL-20 by evaporation or the like while retaining the non-solvent. The non-solvent(s) should be present in a sufficiently low amount to avoid precipitation of the CL-20 out of the solution mixture prior to the addition of CL-20 crystalline seeds and/or evaporation of the solvent(s).

In selecting a CL-20 solvent and CL-20 non-solvent, consideration should be given to the boiling point differential, which preferably is at least 20° C.

Dissolution of the CL-20 into the solvent is preferably conducted at about the same temperature at which the CL-20 is crystallized. Any sequence can be selected for combining the CL-20, the solvent, and the nitrate ester non-solvent, although preferably the CL-20 is added either to the solvent alone or to a mixture of the solvent and nitrate ester non-solvent. The solution is saturated with CL-20, for example, by adding a sufficient volume of non-solvent to the solution to reach the saturation point. Other suitable techniques for saturating the solution include, by way of example, the introduction of additional CL-20 to the solution and/or evaporation of a portion of the solvent from the solution.

As referred to herein, saturated solution encompasses solutions at their saturation points or exceeding their saturation points (i.e., supersaturated), so long as the solution is not supersaturated to the extent that the solution self-nucleates prior to the addition of CL-20 crystal seeds. Excess super-saturation and self-nucleation can cause crystal growth to occur at an extremely high rate, leading to a large number of crystal defects.

In a preferred embodiment of this invention, ε-polymorph CL-20 is crystallized out of the saturated solution by adding ε-polymorph CL-20 seed crystals to the solution and evaporating off the solvent from the solution. The CL-20 crystal seeds are preferably not more than about 30 μm in diameter, more preferably about 2 μm in diameter. To obtain CL-20 crystal seeds in this range, CL-20 crystals can be ground or milled by techniques known in the art, such as a fluid energy mill or a ball mill. The quantity of CL-20 crystal seeds to be added to the saturated solution depends upon the desired crystal sizes of the crystals to be grown. An example of an effective CL-20 crystal size is about 150 μm diameter crystals.

Evaporation of the solvent is preferably done in a azeotropic manner to simultaneously remove any water present in the solution. The azeotropic evaporation of the solvent can be performed subsequent to introducing the CL-20 crystal seeds into crystallization medium or, in the alternative, the sequence of these steps can partially or completely overlap with one another. However, the CL-20 seeds are preferably added to the crystallization medium before the occurrence of excessive super-saturation, which may be caused by evaporation of large amounts of the solvent without simultaneous crystallization of CL-20 out of solution.

High crystallization rates are also avoided by selection of an acceptable crystallization temperature, preferably in a range of from about 25° C. to about 60° C. Operating at temperatures higher than 60° C. can lead to undesirably high rates of crystallization and can lead to the formation of polymorphs other than the epsilon polymorph. On the other hand, evaporating the solvent at temperatures lower than about 25° C. can cause unacceptable amounts of solvent to remain with the CL-20 crystals. Failure to remove a substantial portion of the CL-20 solvent (e.g., about 90 wt % of the CL-20 solvent) can also result in defects in the crystallinity of the CL-20. Selection of the optimum crystallization temperature will vary depending upon the boiling point of the solvent. Another way to facilitate the formation of CL-20 crystals having low defect is to stir the solution at a relatively slow rate during evaporation.

In an alternative, less preferred embodiment of this invention, it is possible to crystallize the CL-20 out of solution without the use of CL-20 crystal seeds. However, the degree of super-saturation of the solution should be maintained low, such as by evaporating off a small portion of the CL-20 solvent. If held for a sufficient period of time, the supersaturated solution will self-nucleate, prompting crystal growth without the addition of CL-20 crystal seeds.

Subsequent to removal of the solvent and crystallization of the CL-20 in the nitrate ester non-solvent, the crystalline CL-20 is separated from the nonsolvent. Separation can be conducted by known solid-liquid separation techniques. For example, the CL-20 crystals can be filtered from the non-solvent, then washed. In the event that a viscous nitrate ester non-solvent is selected, such as poly(glycidyl nitrate), it may be necessary or desirable to lower the viscosity of the non-solvent by diluting the solution in another CL-20 non-solvent. Representative organic liquids for washing the CL-20 crystals and, where appropriate, lowering the viscosity of the nitrate esters, include alcohols such as isopropanol and ethanol, and ethers such as dialkyl ethers, especially diethyl ether. Chlorinated solvents, such as methylene chloride, can also be used, although the chlorinated solvents are less preferred because of the environmental problems raised by their use.

The crystallization method of this invention can be performed on CL-20 made by any one of various techniques known in the art. In this regard, the disclosures of CL-20 synthesis set forth in U.S. Pat. No. 5,693,794 to Nielson, U.S. Pat. No. 5,739,325 to Wardle et al., and EP 0 753 519 A1 are incorporated herein by reference. Another technique for preparing CL-20 comprises nitrolysis of 2,6,8,12-tetraacetyl-2,4,6,8,10,12-hexaazatetracyclo-[$5.5.0.0^{5,9}0^{3,11}$]-dodecane ("TADH") in a mixed acid comprising nitric and sulfuric acids at 85° C. The volumetric ratio of nitric acid to sulfuric acid is preferably about 7:3. The ratio of mixed acid (in milliliters) to TADH (in grams) is preferably about 8:1.

Prior to conducting the crystallization method of this invention, the CL-20 feed can be pre-treated to neutralize any residual acids, such as nitric and sulfuric acids. A representative neutralizing agent is sodium bicarbonate.

The crystallized CL-20 can then be combined with appropriate amounts of binder, plasticizer, fuel, inorganic oxidizers, curative, and/or other ingredients known in the art to make a propellant or explosive. The preparation of propellants and explosives, including the selection of appropriate ingredients and processing steps, is known in the art. Generally, CL-20 constitutes up to about 50% by weight of the total weight of a cured propellant, more preferably not more than about 25% by weight for propellants. Higher concentrations of CL-20 are often desirable for explosives and the like.

The following examples serve to explain embodiments of the present invention in more detail. These examples are not to be construed as being exhaustive or exclusive as to the scope of this invention.

EXAMPLES

Example 1

15 grams of a filtered, saturated CL-20 solution in ethyl acetate were added to 20 grams of poly(glycidyl nitrate) ("PGN") and the whole was stirred at 45° C. until the solution was homogeneous. The ethyl acetate solvent was removed over 45 minutes under vacuum on a rotovapor at 45° C. After the solvent was removed, the PGN was washed off from the resulting crystals with methylene chloride and analyzed by optical microscopy and fourier transform infrared spectroscopy (FTIR). The crystals appeared to be all single crystals of fairly uniform morphology and epsilon polymorph.

Example 2

30 grams of CL-20 were dissolved in 200 grams of ethyl acetate and 120 grams of PGN at 45° C. The ethyl acetate solvent was removed under vacuum on a rotovapor at 45° C. until 140 grams of solution remained. At this point a trace amount of 2 $\mu$m $\epsilon$-polymorph CL-20 seed crystals was added from the tip of a spatula and the evaporation continued. The seed crystals were obtained by grinding epsilon CL-20 in a fluid energy mill. After the solvent was removed, which took about 60 minutes, the PGN was diluted with methylene chloride. The crystals were filtered off and washed with further portions of methylene chloride. ABL impact testing of these crystals was 1.8 cm. Optical microscopy of the crystals showed mostly single crystals of good morphology.

Example 3

20 grams of CL-20 were dissolved in 200 grams of ethyl acetate and 200 grams of PGN at 50° C. The solvent was removed under vacuum on a rotovapor at 50° C. until 250 grams remained. At this point a trace of 2 $\mu$m $\epsilon$-polymorph CL-20 seed crystals was added from the tip of a spatula and the evaporation continued. 30 minutes after the addition of seeds, all of the solvent had been evaporated. The polymer was diluted with methylene chloride. The crystals were filtered off and washed with further portions of methylene chloride. Microscopy showed the crystals to be well formed and "rounded". ABL impact was 3.5 cm. NMR analysis was conducted. Residual polymer was found to be at the limit of detection (<0.05%).

Example 4

100 grams of CL-20 were dissolved in 260 grams of ethyl acetate. 595 grams of PGN were added and the solution warmed to 50° C. At this point a trace of 2 μm ε-polymorph CL-20 seed crystals was added from the tip of a spatula and the solvent evaporated at 50° C. on a rotovapor. 120 minutes after the addition of seeds, all of the solvent had been evaporated. The polymer was diluted with methylene chloride. The crystals were filtered off and washed with further portions of methylene chloride. Microscopy showed the crystals to be well formed. ABL impact was 3.5 cm.

Example 5

The same procedures of Example 4 were followed, but with less PGN (482 grams) and a higher temperature of 60° C. The resulting crystals were of identical optical quality to those from example 4.

Example 6

The same procedures of Example 5 were followed, except 50 grams of CL-20 with 663 grams of PGN and 185 grams of ethyl acetate were mixed at a temperature of 30° C. Under these conditions it took 5 days to evaporate off all of solvent but resulting crystals were of identical optical quality to those from Example 4.

Example 7

25 grams of CL-20 were dissolved in 95 grams of ethyl acetate and 250 grams of PGN at 40° C. in a jacketed round bottomed flask equipped with a mechanical stirrer and a flow of dry air over the surface. A trace of 2 μm ε-polymorph CL-20 seed crystals was added from the tip of a spatula, the stirrer was set at a slow speed, and the solvent evaporated with the air current. Good optical quality crystals were obtained with an ABL impact of 3.5 cm.

Example 8

10 grams of CL-20 were dissolved in 25 grams of ethyl acetate and 50 grams of TEGDN at 42° C. A trace of 2 μm ε-polymorph CL-20 seed crystals was added from the tip of a spatula and the ethyl acetate solvent was removed by evaporation under reduced pressure on a rotovapor. After the solvent was removed, the crystals were filtered off and washed with isopropanol. ABL impact testing of these crystals was 3.5 cm. Optical microscopy of the crystals showed mostly single crystals of good morphology. The crystals were very uniform in size and shape.

Example 9

The same procedures of Example 7 were followed, except with 100 grams of CL-20 dissolved in 300 grams of ethyl acetate mixed with 600 grams of TEGDN. Evaporation was conducted at 50° C. Good optical quality crystals were obtained with an ABL impact of 3.5 cm.

Comparative Example A

In a 1 liter round bottomed flask equipped with a magnetic stir bar, ethyl acetate was added to 50 grams of CL-20 until the CL-20 just dissolved at room temperature. Heptane was slowly added to this solution with gentle stirring until the solution became turbid but no crystallization was apparent. At this point a trace of 2 μm epsilon CL-20 seed crystals was added to the solution. Addition of heptane was continued at a steady rate over 1 hr so that a total of 600 ml of heptane was added. The CL-20 crystals formed in this process were filtered, dried under a current of air and analyzed. FTIR showed them to be epsilon polymorph but microscopy showed them to be of irregular shape with many flaws and voids. ABL impact testing of these crystals was 1.1 cm.

From the above examples and comparative example, it is seen that CL-20 crystallized by the method of this invention consistently exhibited a higher ABL impact measurement and lesser defects than CL-20 crystallized by the comparative example.

The foregoing detailed description of the invention has been provided for the purpose of explaining the principles of the invention and its practical application, thereby enabling others skilled in the art to understand the invention for various embodiments and with various modifications as are suited to the particular use contemplated. This description is not intended to be exhaustive or to limit the invention to the precise embodiments disclosed. Modifications and equivalents will be apparent to practitioners skilled in this art and are encompassed within the spirit and scope of the appended claims.

What is claimed is:

1. A method comprising crystallizing 2,4,6,8,10,12-hexanitro-2,4,6,8,10,12-hexaazatetracyclo[$5.5.0.0^{5,9}0^{3,11}$]-dodecane from a solution comprising at least one organic solvent and at least one nitrate ester non-solvent.

2. The method of claim 1, wherein the nitrate ester non-solvent comprises at least one member selected from the group consisting of poly(glycidyl nitrate) and triethyleneglycol-dinitrate.

3. A method of crystallizing 2,4,6,8,10,12-hexanitro-2,4,6,8,10,12-hexaazatetracyclo[$5.5.0.0^{5,9}0^{3,11}$]-dodecane, comprising:

combining 2,4,6,8,10,12-hexanitro-2,4,6,8,10,12-hexaazatetracyclo[$5.5.0.0^{5,9}0^{3,11}$]-dodecane, at least one organic solvent present in an effective amount to completely dissolve the 2,4,6,8,10,12-hexanitro-2,4,6,8,10,12-hexaazatetracyclo[$5.5.0.0^{5,9}0^{3,11}$]-dodecane into solution, and at least one nitrate ester non-solvent which is miscible with the solvent to form a solution;

saturating the solution;

adding 2,4,6,8,10,12-hexanitro-2,4,6,8,10,12-hexaazatetracyclo[$5.5.0.0^{5,9}0^{3,11}$]-dodecane crystalline seeds to the saturated solution;

evaporating the solvent from the saturated solution while simultaneously growing 2,4,6,8,10,12-hexanitro-2,4,6,8,10,12-hexaazatetracyclo[$5.5.0.0^{5,9}0^{3,11}$]-dodecane crystals from the saturated solution onto the crystalline seeds; and separating the nitrate ester non-solvent and non-evaporated remnants, if any, of the solvent from the crystals.

4. The method of claim 3, wherein the nitrate ester non-solvent comprises poly(glycidyl nitrate).

5. The method of claim 3, wherein the nitrate ester non-solvent comprises triethyleneglycol-dinitrate.

6. The method of claim 3, wherein the nitrate ester non-solvent comprises at least one member selected from the group consisting of butanetrioltrinitrate and diglycerol tetranitrate.

7. The method of claim 3, wherein the solvent comprises at least one alkyl acetate.

8. The method of claim 7, wherein the alkyl acetate comprises ethyl acetate.

9. The method of claim 3, wherein the solvent comprises at least one member selected from the group consisting of a ketone, a cyclic ether, nitromethane, and acetonitrile.

10. The method of claim 3, wherein said combining and said saturating of the solution are performed simultaneous by dissolving 2,4,6,8,10,12-hexanitro-2,4,6,8,10,12-hexaazatetracyclo[5.5.0.0$^{5,9}$0$^{3,11}$]-dodecane into the CL-20 solvent and then adding an effective amount of the nitrate-ester non-solvent to form the saturated solution.

11. The method of claim 3, wherein said saturating of the solution comprises evaporating off the CL-20 solvent until the saturated solution is formed.

12. The method of claim 3, wherein said saturating of the solution comprises adding the 2,4,6,8,10,12-hexanitro-2,4,6,8,10,12-hexaazatetracyclo[5.5.0.0$^{5,9}$0$^{3,11}$]-dodecane crystalline seeds to the solution until the solution is saturated.

13. The method of claim 3, wherein said evaporating of the solvent is conducted in a temperature range of from about 25° C. to about 60° C.

14. The method of claim 3, wherein a weight ratio of the nitrate ester non-solvent to CL-20 is in a range of from about 5:1 to about 8:1.

15. A method of crystallizing 2,4,6,8,10,12-hexanitro-2,4,6,8,10,12-hexaazatetracyclo[5.5.0.0$^{5,9}$0$^{3,11}$]-dodecane comprising:

combining 2,4,6,8,10,12-hexanitro-2,4,6,8,10,12-hexaazatetracyclo[5.5.0.0$^{5,9}$0$^{3,11}$]-dodecane, at least one organic solvent present in an effective amount to completely dissolve the 2,4,6,8,10,12-hexanitro-2,4,6,8,10,12-hexaazatetracyclo[5.5.0.0$^{5,9}$0$^{3,11}$]-dodecane into solution, and at least one nitrate ester non-solvent which is miscible with the solvent to form a solution, the nitrate ester non-solvent comprising at least one member selected from the group consisting of poly(glycidyl nitrate) and triethylene glycol dinitrate;

saturating the solution;

adding 2,4,6,8,10,12-hexanitro-2,4,6,8,10,12-hexaazatetracyclo[5.5.0.0$^{5,9}$0$^{3,11}$]-dodecane crystalline seeds to the saturated solution;

evaporating the solvent from the saturated solution while simultaneously growing 2,4,6,8,10,12-hexanitro-2,4,6,8,10,12-hexaazatetracyclo[5.5.0.0$^{5,9}$0$^{3,11}$]-dodecane crystals from the saturated solution onto the crystalline seeds; and separating the nitrate ester non-solvent and non-evaporated remnants, if any, of the solvent from the crystals.

16. The method of claim 15, wherein the nitrate ester non-solvent further comprises at least one member selected from the group consisting of butanetrioltrinitrate and diglycerol tetranitrate.

17. The method of claim 15, wherein the solvent comprises at least one alkyl acetate.

18. The method of claim 17, wherein the alkyl acetate comprise ethyl acetate.

19. The method of claim 15, wherein the solvent comprises at least one member selected from the group consisting of a ketone, a cyclic ether, nitromethane, and acetonitrile.

20. The method of claim 15, wherein said combining and said saturating of the solution are performed simultaneous by dissolving 2,4,6,8,10,12-hexanitro-2,4,6,8,10,12-hexaazatetracyclo[5.5.0.0$^{5,9}$0$^{3,11}$]-dodecane into the CL-20 solvent and then adding an effective amount of the nitrate ester non-solvent to form the saturated solution.

21. The method of claim 15, wherein said saturating of the solution comprises evaporating off the CL-20 solvent until the saturated solution is formed.

22. The method of claim 15, wherein said saturating of the solution comprises adding the 2,4,6,8,10,12-hexanitro-2,4,6,8,10,12-hexaazatetracyclo[5.5.0.0$^{5,9}$0$^{3,11}$]-dodecane crystalline seeds to the solution until the solution is saturated.

23. The method of claim 15, wherein said evaporating of the solvent is conducted in a temperature range of from about 25° C. to about 60° C.

24. The method of claim 15, wherein a weight ratio of the nitrate ester non-solvent to CL-20 is in a range of from about 5:1 to about 8:1.

25. A method of crystallizing 2,4,6,8,10,12-hexanitro-2,4,6,8,10,12-hexaazatetracyclo[5.5.0.0$^{5,9}$0$^{3,11}$]-dodecane, comprising:

combining 2,4,6,8,10,12-hexanitro-2,4,6,8,10,12-hexaazatetracyclo[5.5.0.0$^{5,9}$0$^{3,11}$]-dodecane, at least one organic solvent present in an effective amount to completely dissolve the 2,4,6,8,10,12-hexanitro-2,4,6,8,10,12-hexaazatetracyclo[5.5.0.0$^{5,9}$0$^{3,11}$]-dodecane into solution, and at least one nitrate ester non-solvent which is miscible with the solvent to form a solution;

supersaturating the solution and holding the supersaturated solution until crystal growth commences by self-nucleation;

evaporating the solvent from the supersaturated solution while simultaneously growing 2,4,6,8,10,12-hexanitro-2,4,6,8,10,12-hexaazatetracyclo[5.5.0.0$^{5,9}$0$^{3,11}$]-dodecane crystals from the supersaturated solution onto the crystalline seeds; and separating the nitrate ester non-solvent and non-evaporated remnants, if any, of the solvent from the crystals.

26. The method of claim 25, wherein the nitrate ester non-solvent comprises at least one member selected from the group consisting of poly(glycidyl nitrate) and triethyleneglycol-dinitrate.

* * * * *